(12) United States Patent
Boomsma et al.

(10) Patent No.: US 9,011,432 B2
(45) Date of Patent: Apr. 21, 2015

(54) IRRIGATION CATHETER DEVICE AND ABLATION SYSTEM

(71) Applicant: VascoMed GmbH, Binzen (DE)

(72) Inventors: Kevin Boomsma, Thalwil (CH); Andreas Kiefer, Denzlingen (DE); Ralf Kaufmann, Loerrach (DE); Ingo Weiss, Berlin (DE); Stefan Knorr, Berlin (DE)

(73) Assignee: VascoMed GmbH, Binzen (DE)

( * ) Notice: Subject to any disclaimer, the term of this patent is extended or adjusted under 35 U.S.C. 154(b) by 233 days.

(21) Appl. No.: 13/693,518

(22) Filed: Dec. 4, 2012

(65) Prior Publication Data

US 2013/0150805 A1    Jun. 13, 2013

Related U.S. Application Data

(60) Provisional application No. 61/569,803, filed on Dec. 13, 2011.

(51) Int. Cl.
| | | |
|---|---|---|
| *A61B 18/18* | (2006.01) | |
| *A61M 3/02* | (2006.01) | |
| *A61B 18/14* | (2006.01) | |
| *A61B 18/00* | (2006.01) | |
| *A61B 19/00* | (2006.01) | |

(52) U.S. Cl.
CPC .......... *A61M 3/0279* (2013.01); *A61B 18/1492* (2013.01); *A61B 2018/00863* (2013.01); *A61B 2019/464* (2013.01); *A61B 2019/467* (2013.01); *A61B 2218/002* (2013.01)

(58) Field of Classification Search
CPC .................................................... A61M 3/0279
USPC ............................................................ 606/41
See application file for complete search history.

(56) References Cited

U.S. PATENT DOCUMENTS

2008/0071267 A1    3/2008  Wang et al.
2008/0161794 A1*   7/2008  Wang et al. ..................... 606/41

FOREIGN PATENT DOCUMENTS

EP    2 343 022    7/2011
EP    2 380 517    10/2011

OTHER PUBLICATIONS

Partial European Search Report on European Patent Application No. EP 12 19 2916, dated Mar. 13, 2013 (5 pages).

* cited by examiner

*Primary Examiner* — Robert N Wieland
(74) *Attorney, Agent, or Firm* — Buchanan Ingersoll & Rooney PC

(57) ABSTRACT

An irrigation catheter device, in particular an ablation catheter, including a catheter body in which a central lumen extends from a proximal region into a distal region, wherein a large number of irrigation channels extend away from the lumen, the outlet openings of which out of the catheter body are distributed across the distal end region thereof, wherein sensors are assigned to the central lumen and/or the individual irrigation channels for pressure measurement and/or to measure the flow velocity, to which evaluation means are connected, which are designed to determine the open or closed state of a portion of the irrigation channels on the basis of measured values registered by the sensors.

16 Claims, 5 Drawing Sheets

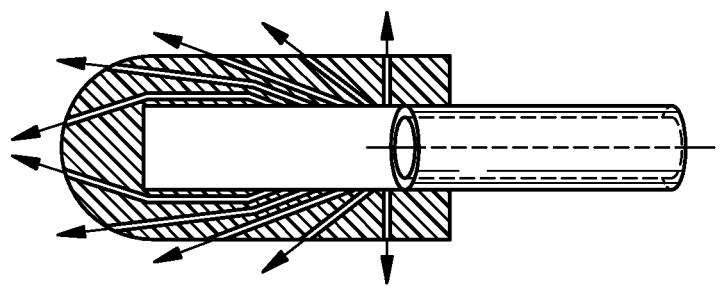
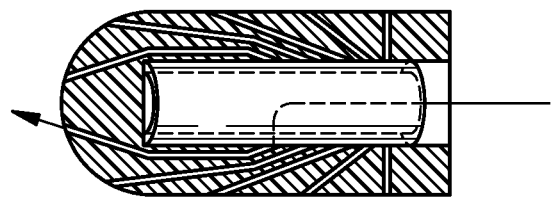
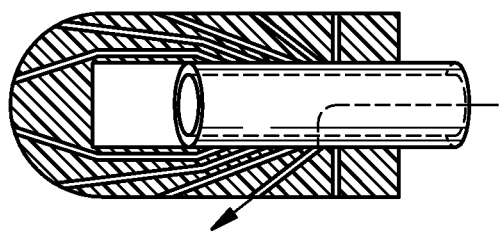
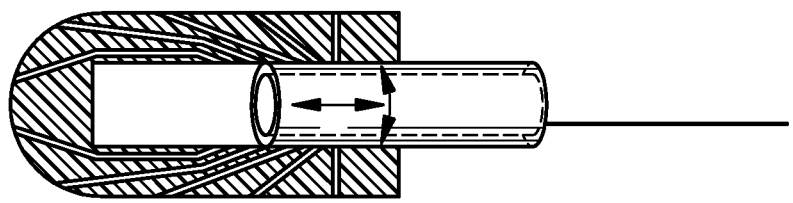
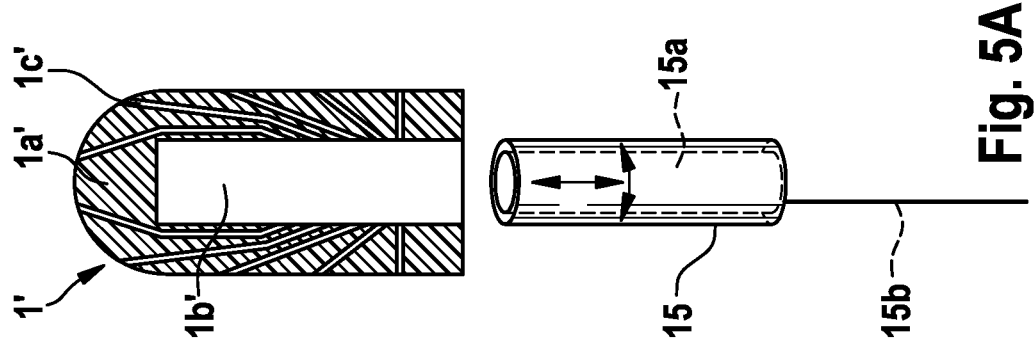

IRRIGATION CATHETER DEVICE AND ABLATION SYSTEM

CROSS-REFERENCE TO RELATED APPLICATIONS

This patent application claims the benefit of U.S. Provisional Patent Application No. 61/569,803, filed on Dec. 13, 2011, which is hereby incorporated by reference in its entirety.

TECHNICAL FIELD

The present invention relates to an irrigation catheter device and, in particular, an ablation catheter, comprising a catheter body in which a central lumen extends from a proximal region into a distal region, wherein a large number of irrigation channels extend away from the lumen, the outlet openings of which out of the catheter body are distributed across the distal end region thereof. The present invention furthermore relates to an ablation system.

BACKGROUND

Ablation catheters, which can be used to necrotize or ablate bodily tissue in vessels or hollow organs at an exact point using electrothermal means and with all of the advantages of minimally invasive surgery, have been known and used in clinical applications for a long time. They are used, inter alia, to remove selected regions of excitable cardiac tissue within the scope of treatment of cardiac arrhythmias. To ensure successful use thereof, it is of considerable—and often decisive—significance that the operating surgeon be able to assess the quality of the contact between an electrode mounted on the distal catheter end or another ablation element and the bodily tissue.

Ablation catheters are also known, which are provided with outlet openings (irrigation openings) by way of irrigation channels in the distal region, which are intended for delivering fluids to the treatment site in order to cool surrounding tissue at this point or, optionally, to wash away ablated tissue components. The irrigation channels are connected, by way of a central lumen in the catheter body at the proximal end of the catheter, to a pump which is used to supply fluid from an irrigation fluid reservoir. Such an ablation catheter, which is referred to in the following as an irrigation catheter device, is described in European Patent No. EP 2 343 022, for example.

The present invention is directed toward overcoming one or more of the above-identified problems. A problem addressed by the present invention is that of providing an improved irrigation catheter device which can be used simultaneously as means for determining the presence and the quality of a contact with surrounding bodily tissue.

SUMMARY

A problem is solved by an irrigation catheter device having the features of the independent claim(s). Advantageous developments of the inventive idea are the subject matter of the dependent claims. Moreover, an ablation device having the features of claim 14 is provided.

The present invention incorporates the idea of using comparative pressure measurements and/or flow measurements in/at the irrigation channels to determine the quality of the tissue contact, and to provide means suitable therefor in/at the irrigation and ablation catheter. The pressure conditions change due to the closure of individual irrigation channels by adjacent tissue. An interpretation principle contemplated by the present invention is that the more irrigation channels that are throttled by tissue, the greater the contact surface/electrically active surface is of the electrode. Since the geometry of the electrode and the irrigation channels are known, the tissue contact can be localized (e.g., contact at the tip, lateral contact, etc.). The contact angle could likewise be determined in this manner.

In the irrigation catheter device provided, sensors are assigned to the central lumen and/or the individual irrigation channels for pressure measurement and/or to measure the flow velocity. Evaluation means are connected to the sensors, which are designed to determine the open or closed state of a portion of the irrigation channels on the basis of measured values registered by the sensors.

The measured quantity is ascertained using one or more pressure sensors. Three connections of the measurement sensors are feasible, in particular.

1. The pressure change is measured using one pressure sensor in the irrigation system, which registers the change in the entire irrigation system. The quality of the contact is deduced by way of comparison with a reference measurement.
   a. Variable pressure drop is measured at one point.
   b. Specified flow rate.
   c. No ambiguity due to variable diameters of nozzles.
2. The measurement of the pressure change takes place simultaneously for a plurality of irrigation channel connections. This makes it possible to determine the state with great accuracy.
   a. Nozzles open: Measurements of static pressure are equal.
   b. Nozzles closed: Measurements of static pressure are different. Static pressure in closed channels is greater.
   c. Dynamic pressure remains constant in the feed tube since the flow rate is specified.
   d. Digital measurement
3. Rotating irrigation head, and mechanical closing element (multiplexer).
   a. Search operation: Which nozzles are clogged?
   b. Irrigation operation: All nozzles are open.

According to the first of the stated modes of operation, in one embodiment of the irrigation catheter device, a lumen sensor is assigned only to the central lumen, and comparator means are provided in the evaluation means to compare currently registered measured values with stored comparison values for the possible combinations of open and closed states of the irrigation channels.

According to an embodiment of the second mode of operation, one irrigation channel sensor is assigned to one irrigation channel or a group of irrigation channels having outlet openings which are adjacent to one another. In the evaluation means, comparator means for comparing currently registered measured values with stored comparison values of open and closed states of the irrigation channel, or the group of irrigation channels are provided, which are assigned to the particular irrigation channel sensor. In a further embodiment of this mode of operation, one lumen sensor is assigned to the central lumen, and one irrigation channel sensor is assigned to one irrigation channel or a group of irrigation channels having adjacently disposed outlet openings, and comparator means for comparing currently registered measured values of the irrigation channel sensors with currently registered measured values of the lumen sensor are provided in the evaluation means.

According to the third above-noted mode of operation, a controllable mechanical closing element for selectively opening an irrigation channel outlet, or a group of irrigation channel outlets of irrigation channels having adjacently disposed outlet openings, is provided in the lumen. A closing element sensor is assigned to this closing element, and comparator means are provided in the evaluation means for comparing currently registered measured values with stored measured values for an open and closed state, each assigned to a selectively opened irrigation channel outlet or a group of opened irrigation channel outlets.

In one design of this embodiment, the mechanical closing element is in the form of a hollow cylinder having wall openings disposed in accordance with the position of an irrigation channel outlet or the positions of a group of irrigation channel outlets. In particular, the closing element is made of high-grade, flexible material. In a further embodiment, a force-transmission element, in particular a wire or tube, is attached to the proximal end of the closing element for control thereof.

For all of the variants mentioned, it makes sense to measure the intracardial pressure as the reference pressure, if not required to obtain reliable results. To this end, a separate comparison measurement channel is provided, which extends from the distal end region to the proximal end of the catheter body, to which a comparison pressure sensor is assigned for detection of an internal pressure value of a vessel or hollow organ. The comparison pressure is therefore measured by way of a channel in the catheter that leads outwardly.

In a further embodiment, the, or each, irrigation catheter sensor is designed to register the dynamic pressure and/or the lumen sensor is designed to register the static pressure. In yet another embodiment of the present invention, the particular measuring transducer of the sensor, or at least a portion of the sensor, is disposed on the proximal end of the catheter body outside of the patient.

The ablation system provided herein comprises, in addition to an ablation catheter designed according to at least one portion of the aspects mentioned above, a control device having a processing and display device which is designed to process the evaluation results for determination of the quality of the tissue contact of an ablation element of the ablation catheter, and to provide a corresponding display. In practical application, the measured values are evaluated by way of a measurement card and are visualized on, for example, a PC, notebook or tablet computer equipped with the appropriate software, in the sense of clear handling instructions for the operating surgeon ("good contact—ablation okay; poor contact—ablation not okay").

Further features, aspects, objects, advantages, and possible applications of the present invention will become apparent from a study of the exemplary embodiments and examples described below, in combination with the figures, and the appended claims.

DESCRIPTION OF THE DRAWINGS

Advantages and useful features of the present invention will also become apparent from the descriptions that follow of exemplary embodiments of the present invention, with reference to the figures. The figures show:

FIGS. 5A-5E show schematic longitudinal sectional views of the catheter head of a further embodiment of an ablation catheter according to the present invention.

DETAILED DESCRIPTION

Figure 1:
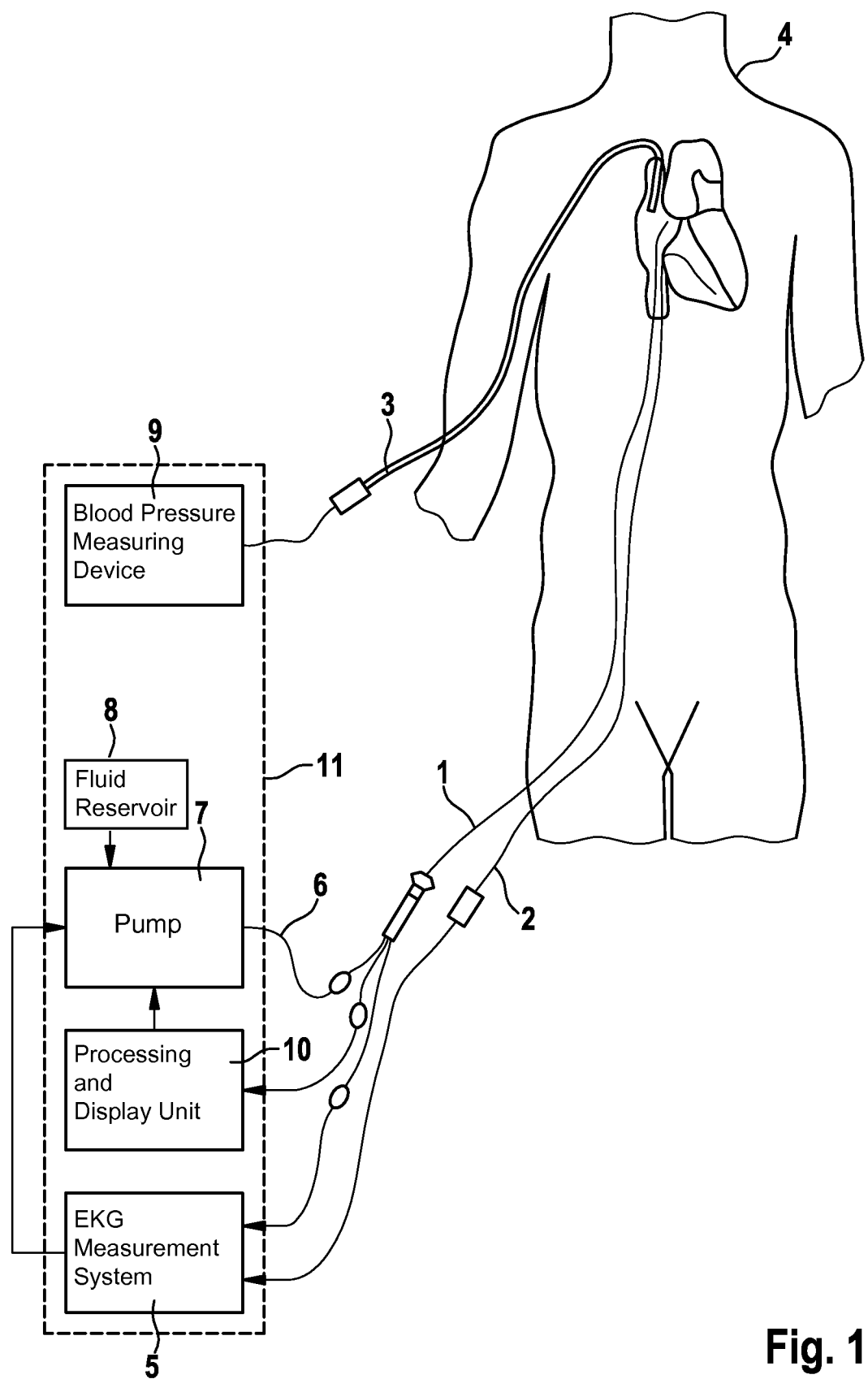
FIG. 1 shows a schematic depiction of an embodiment of an ablation system according to the present invention in the manner of a block diagram.

FIG. 1 shows, in the manner of a block diagram, an ablation system which comprises, in addition to an ablation catheter 1, at least one further EP diagnostic catheter 2 and a blood pressure measurement catheter 3, the distal ends of which are positioned in the heart of a patient 4. The ablation catheter 1 and the EP diagnostic catheter 2 are connected to an EKG measurement system 5. The ablation catheter 1 comprises (to be explained in greater detail below) irrigation channels and openings which are intended to be capable of delivering fluid to the ablation site in order to cool the bodily tissue at this point. To this end, the ablation catheter 1 is connected to an irrigation fluid tube 6 which is connected, by way of a pump 7, to a fluid reservoir 8.

The proximal end of the ablation catheter 1 is furthermore connected to a processing and display unit 10, which is designed to process and display the results of pressure measurements and flow measurements carried out in or at the ablation catheter 1 in order to determine the quality of contact between the distal end and adjacent bodily tissue. The EKG measurement system 5 and the processing and display unit 10 can be connected, via control signal lines, to the pump 7 and, in combination therewith and with the fluid reservoir 8 and a blood pressure measuring device 9 connected to the blood pressure measurement catheter 3, forms a therapy device 11 of the inventive system.

Figure 2:
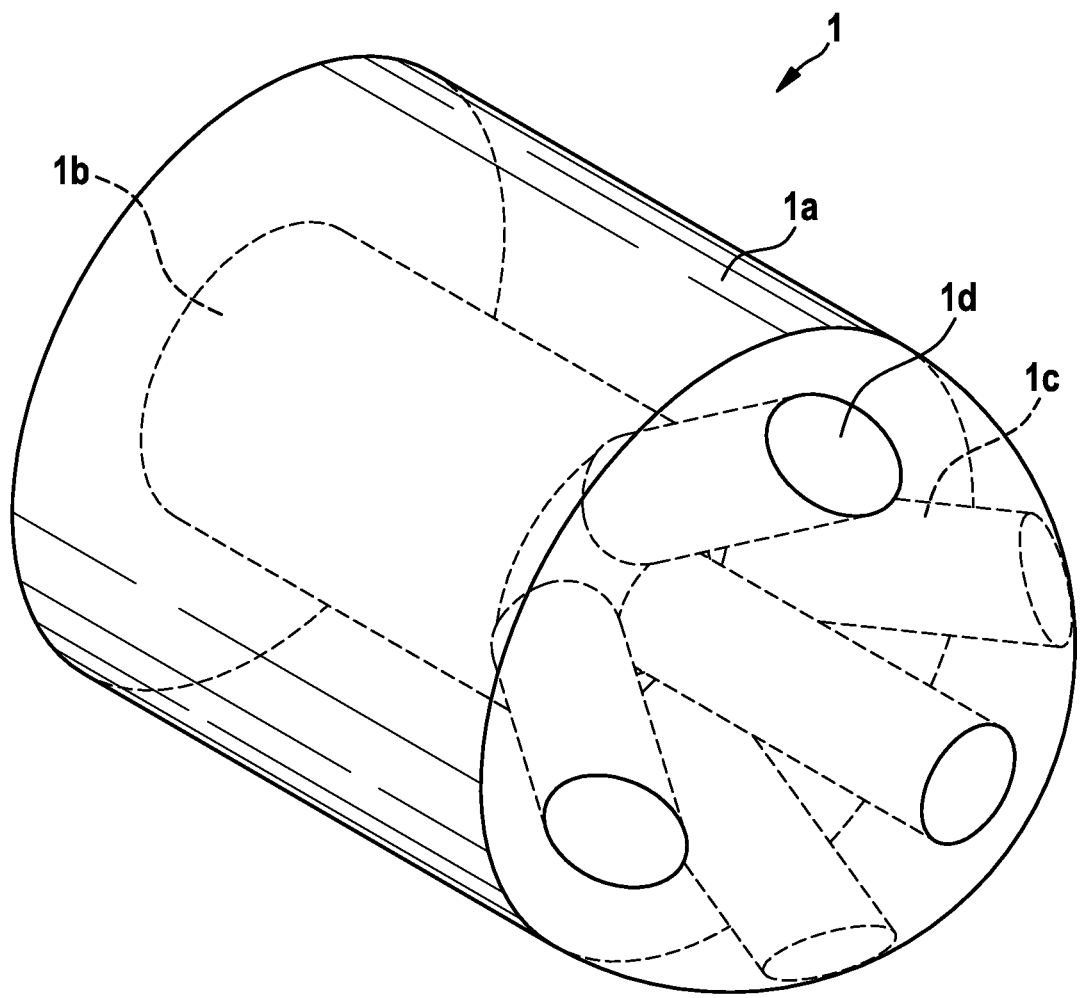
FIG. 2 shows a perspective depiction ("hidden line view") of the distal end of an embodiment of the irrigation catheter device according to the present invention.

FIG. 2 shows the distal end of the ablation catheter 1 and the "catheter head" 1a thereof in such a way that only the elements essential to the explanation of the present invention are shown, namely, a central lumen 1b and a plurality of irrigation channels 1c extending away therefrom, each of which has an outlet opening 1d on the outer surface of the catheter head 1a.

Figure 3A:
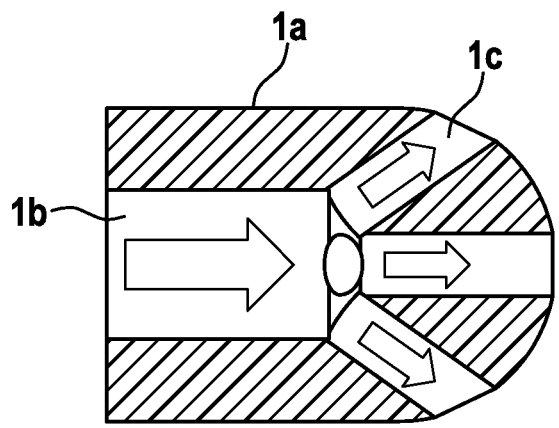
FIGS. 3A-3C show views to explain the mode of operation of the irrigation catheter device according to the present invention.
Figure 3B:
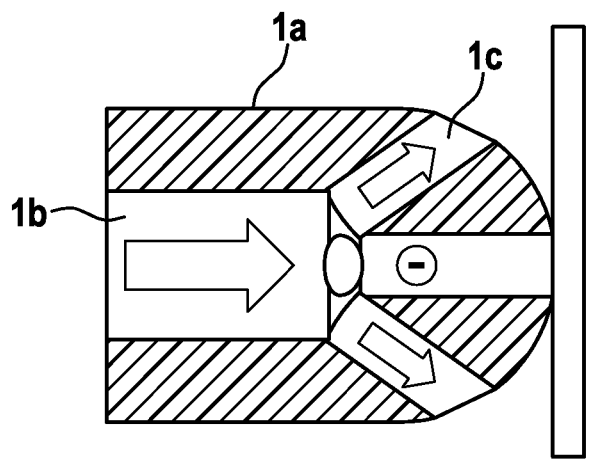
Figure 3C:
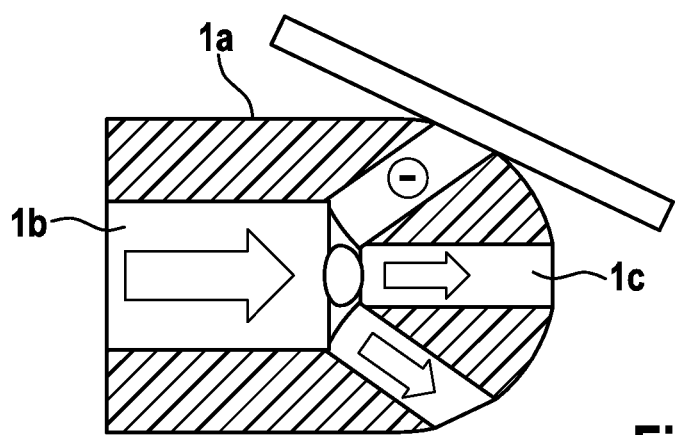

This labeling is also used in FIGS. 3A to 3C, which schematically depict how a contact of the catheter head 1a with surrounding bodily tissue in a certain angular position results in closure of a portion of the outlet openings of the irrigation channels 1c. It is immediately clear that such a closure results in an increase in the pressure that can be measured in the particular irrigation channel, and/or in a reduction in the measurable flow rate (e.g., down to zero).

The contact angle is determined by differentiation of the measured pressure drop at a specified flow rate. If the flow rate remains constant, the pressure drop is dependent only upon the combination of the open irrigation channels in the catheter head. The lowest pressure drop given a constant flow rate is measured when all irrigation channels are open. The closure of an irrigation channel at a constant flow rate in the catheter increases the flow rate in the irrigation channels that remain open, and the pressure drop measured in the catheter tube (or at the pump) is therefore higher. The increase in the pressure drop (measured against the pressure in the heart) in the catheter tube generally indicates contact of the catheter head with tissue.

The irrigation channels located in the catheter head can have different diameters and/or lengths, depending on the orientation in the head, so that the closure of an irrigation channel at a certain contact angle creates a unique combination of open irrigation channels which, in turn, indicates a unique pressure drop at a constant flow rate in the catheter.

The pressure drop in the catheter tube can be calculated using the following formula (1):

$$\Delta P = \frac{128 \mu L Q}{\pi d^4} \quad (1)$$

in which:
ΔP: pressure drop (mbar)
μ: dynamic viscosity, water=0.8 e$^{-3}$ (Pa–s).
L: length of the channel (mm).
Q: flow rate, water=20 ml/min.
d: diameter of the channel (mm).

In the formula (1) shown above, the dependence of pressure drop on diameter and on the length of a channel is clear. The so-called "minor losses" of the pressure drop were not accounted for in this calculation of the pressure drop. "Minor losses" include, for example, the pressure drops caused by constrictions, redirections, expansions and outlet openings in the channel.

The pressure drop in the irrigation channels located in the catheter head is calculated in a different way, however. Since the majority of the pressure drop is caused by redirections, constrictions, etc., the formula (2) for "minor losses" is used.

$$\Delta P = 0.5 \xi v^2 \quad (2)$$

in which:
ξ: coefficient of pressure drop.
v: mean flow velocity (ml/min).

Table 1 show below presents dimensions, for example purposes of a hypothetical catheter having three different flow sections, with coefficients of pressure drop as examples.

TABLE 1

Dimensions of the flow sections in the catheter or catheter head.

| | Catheter tube | Irrigation channel in the center | Irrigation channel on the side |
|---|---|---|---|
| Number | 1 | 1 | 4 |
| Diameter (mm) | 1.00 | 0.40 | 0.30 |
| Length (mm) | 1500 | — | — |
| Coefficient of pressure drop (—) | — | 1.0e$^4$ | 1.0e$^4$ |

The pressure drops of the individual flow sections were calculated for three scenarios and are listed in Table 2 below. In all of the scenarios, the flow rate is 20 ml/min. The three scenarios are:
 1. All irrigation channels open.
 2. Irrigation channels in the center closed due to contact with tissue by 90°.
 3. An irrigation channel installed on the side is closed due to contact with tissue by approximately 45°.

TABLE 2

Calculation of the pressure drops in three scenarios.

| Pressure drop (mbar) | Scenario 1 | Scenario 2 | Scenario 3 |
|---|---|---|---|
| Catheter tube | 163.0 | 163.0 | 163.0 |
| Irrigation channel in the center | 33.3 | -closed- | 48.7 |
| Irrigation channel on the side | 33.3 | 69.5 | 1 channel closed |
| Total | 196.3 | 232.5 | 211.7 |

Table 2 above clarifies the basic principles:
 1. The pressure drop in the catheter tube remains constant because the flow rate is specified by the pump. If all channels are open, the pressure drop measured at the pump is 196.3 mbar.
 2. Blocking the center channel (Scenario 2) increases the pressure drop measured at the pump to 232.5 mbar. This scenario corresponds to a contact with tissue by 90°.
 3. Blocking one of the four irrigation channels attached to the side likewise increases the pressure drop measured at the pump, although to a lesser extent, to only 211.7 mbar. This scenario corresponds to lateral contact with tissue by approximately 45°.

Since the pressure drop is clearly differentiated in these scenarios, it becomes unambiguously clear only by reference to the pressure drop that was determined whether the contact with the tissue is by 90° or 45°.

The coefficients of pressure drop of the irrigation channels can be fine-tuned to generate the maximum pressure differential in order to clarify the signal that is registered. The tuning can take place, for example, by installing constrictions or redirections.

To determine the tissue contact between the catheter tip and the surrounding tissue, in a further exemplary embodiment, the flow velocity in the irrigation channels is monitored during the irrigation process: In the presence of good tissue contact, the irrigation channels in the contact zone are closed and the flow velocity in the corresponding channels is markedly lower than in the channels that are not closed. It is therefore possible to determine the position and size of the tissue contact on the basis of the flow velocities in the irrigation channels.

In principle, many methods are available for measuring pressure, although not all can be reasonably miniaturized. Methods in which the actual velocity measurement can be carried out outside of the catheter are particularly suitable.

This is possible using a pressure measurement method, for instance: According to the Bernoulli equation, the flow velocity can be determined on the basis of the pressure differential between static and dynamic pressure. This effect is used in the Pitot tube, a well-known pressure measurement instrument.

Another procedure makes sense in the catheter, to avoid constricting the thin irrigation channels unnecessarily. The static pressure can be measured, rather than directly with a Pitot tube, indirectly by way of the known flow rate and the measurement of the dynamic pressure shortly before the branching. Shortly after the branching, the dynamic pressure can be measured in the irrigation channels once more. If both measurement points are located close to one another, the pressure drop is negligibly small.

Figure 4:
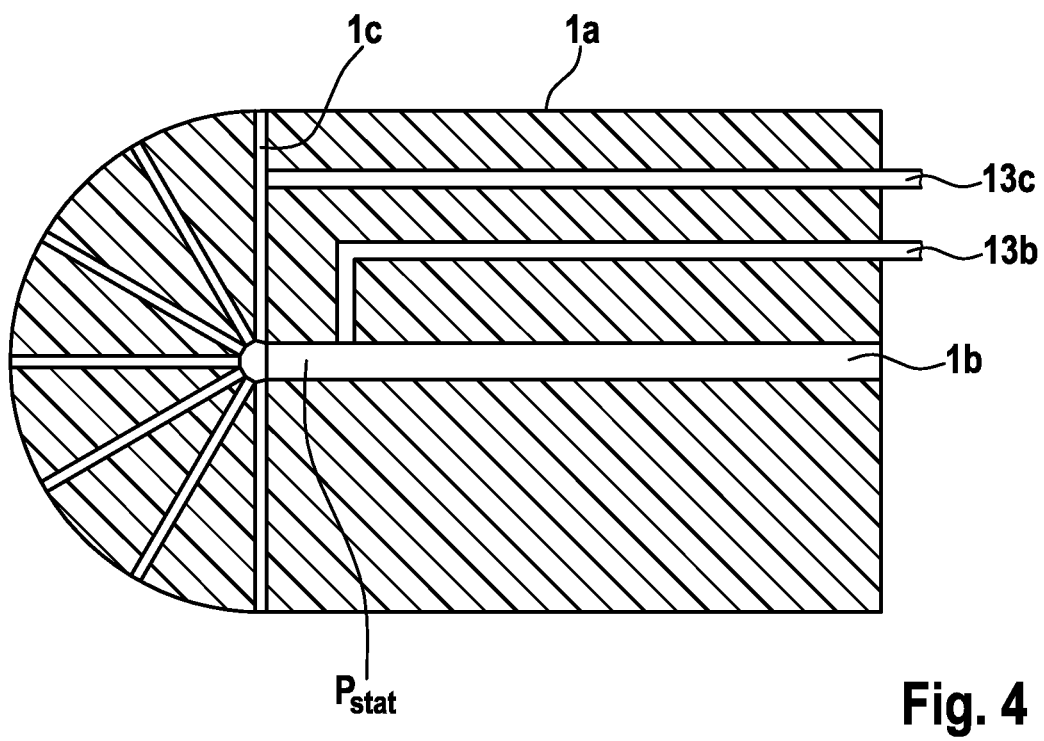
FIG. 4 shows a schematic, longitudinal sectional view of the catheter head with indications of the measurement principle.

In FIG. 4, the catheter head 1a is shown once more, symbolically, which comprises a central lumen 1b for irrigation-channel supply, which branches into different irrigation channels 1c. The static pressure is measured by way of a dynamic pressure measurement using fluid column 1b with consideration for the known flow rate (from the proximal catheter end). The pressure is determined in the individual irrigation channels using a plurality of fluid columns 13c, although only one is shown, as an example. The flow velocities in each channel can be determined on the basis of the dynamic pressures in the irrigation channels that are measured, and the static pressure $P_{stat}$ before the branching. All pressure transducers for the liquid column 13b and the liquid columns 13c are located outside of the patient.

Proceeding from the above-described concept, the liquid columns of a plurality of adjacent irrigation channels can be combined in order to reduce the number of liquid channels in the catheter. Measurement therefore no longer takes place per channel, but rather per area. For instance, five areas can be the tip and four radially disposed proximal areas.

FIGS. 5A to 5E show, as a further exemplary embodiment of the present invention, the design and various states of use of the catheter head of a further ablation catheter 1'. Reference characters are indicated only in FIG. 5A, for clarity. The reference characters are based on those used in FIGS. 2 to 3C.

A mechanical closing element 15 having the basic shape of a hollow cylinder is provided in the catheter head 1a', which fits into the lumen 1b' and comprises an opening 15a which can be moved into overlap with the outlet of a desired irrigation channel 1c' out of the lumen 1b' by way of a positioning wire 15b (which can be handled from the proximal catheter end) installed on the proximal end of the hollow cylinder 15.

Examples for the selection of individual irrigation channels using the closing element 15 are shown in FIGS. 5B to 5D. FIGS. 5C and 5D each show a liquid flow out of the lumen 1b' by way of a selected irrigation channel and the outlet opening thereof into the region distal of the catheter tip. FIG. 5E shows a position of the closing element 15, in which all irrigation channels 1c' are acted upon with irrigation fluid, and so irrigation fluid emerges from all outlet openings.

The closing device 15 is positioned using rotational motions and advancing motions in a number of steps corresponding to the number of irrigation channels in each case in such a manner that one irrigation channel is switched to passage ("active") in each case, while all other irrigation channels remain closed. A pressure or flow measurement is carried out in each of the search positions to determine whether the selected irrigation channel is open or closed. To then ensure that the usual irrigation operation can take place by way of all irrigation channels, the closing element is brought into the state shown in FIG. 5E.

The embodiments of the present invention are not limited to the above-described examples and emphasized aspects but, rather, are possible in a large number of modifications that lie within the scope of handling by a person skilled in the art.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range.

We claim:

1. An irrigation catheter device, in particular an ablation catheter, comprising:
    a catheter body in which a central lumen extends from a proximal region into a distal region, wherein a plurality of irrigation channels extend away from the lumen, the outlet openings of which out of the catheter body are distributed across the distal end region thereof;
    at least one sensor for pressure measurement or to measure flow velocity; and
    evaluation means connected to the at least one sensor,
    wherein the at least one sensor is assigned to the central lumen and/or the individual irrigation channels for pressure measurement therein or to measure the flow velocity therein, to which the evaluation means are connected, which are designed to determine the open or closed state of a portion of the irrigation channels on the basis of measured values registered by the sensors,
    wherein the at least one sensor comprises a lumen sensor assigned only to the central lumen, and
    the irrigation catheter device further comprising comparator means provided in the evaluation means to compare currently registered measured values with stored comparison values for the possible combinations of open and closed states of the irrigation channels.

2. The irrigation catheter device according to claim 1, further comprising one irrigation channel sensor assigned to one irrigation channel, and, wherein in the evaluation means, the comparator means for comparing currently registered measured values with stored comparison values of open and closed states of the irrigation channel are provided, which are assigned to the particular irrigation channel sensor.

3. An irrigation catheter device, in particular an ablation catheter, comprising:
    a catheter body in which a central lumen extends from a proximal region into a distal region, wherein a plurality of irrigation channels extend away from the lumen, the outlet openings of which out of the catheter body are distributed across the distal end region thereof;
    at least one sensor for pressure measurement or to measure flow velocity; and
    evaluation means connected to the at least one sensor,
    wherein the at least one sensor is assigned to the central lumen and/or the individual irrigation channels for pressure measurement therein or to measure the flow velocity therein, to which the evaluation means are connected, which are designed to determine the open or closed state of a portion of the irrigation channels on the basis of measured values registered by the sensors,
    wherein the at least one sensor comprises one lumen sensor assigned to the central lumen, and one irrigation channel sensor assigned to one irrigation channel, and
    the irrigation catheter device further comprising comparator means provided in the evaluation means for comparing currently registered measured values of the irrigation channel sensors with currently registered measured values of the lumen sensor.

4. The irrigation catheter device according to claim 1, further comprising one irrigation channel sensor assigned to a group of irrigation channels having outlet openings which are adjacent to one another, and, wherein in the evaluation means, the comparator means for comparing currently registered measured values with stored comparison values of open and closed states of the group of irrigation channels are provided, which are assigned to the particular irrigation channel sensor.

5. An irrigation catheter device, in particular an ablation catheter, comprising:
    a catheter body in which a central lumen extends from a proximal region into a distal region, wherein a plurality of irrigation channels extend away from the lumen, the outlet openings of which out of the catheter body are distributed across the distal end region thereof;

at least one sensor for pressure measurement or to measure flow velocity; and evaluation means connected to the at least one sensor, wherein the at least one sensor is assigned to the central lumen and/or the individual irrigation channels for pressure measurement therein or to measure the flow velocity therein, to which the evaluation means are connected, which are designed to determine the open or closed state of a portion of the irrigation channels on the basis of measured values registered by the sensors, wherein the at least one sensor comprises one lumen sensor assigned to the central lumen, and one irrigation channel sensor assigned to a group of irrigation channels having adjacently disposed outlet openings, and the irrigation catheter device further comprising comparator means provided in the evaluation means for comparing currently registered measured values of the irrigation channel sensors with currently registered measured values of the lumen sensor.

6. The irrigation catheter device according to claim 1, further comprising:

a controllable mechanical closing element for selectively opening an irrigation channel outlet or a group of irrigation channel outlets of irrigation channels having adjacently disposed outlet openings is provided in the lumen, and a closing element sensor assigned to the closing element, and wherein the comparator means are provided in the evaluation means for comparing currently registered measured values with stored measured values for an open and closed state, each assigned to a selectively opened irrigation channel outlet or a group of opened irrigation channel outlets.

7. The irrigation catheter device according to claim 6, wherein the mechanical closing element is in the form of a hollow cylinder having wall openings disposed in accordance with the position of an irrigation channel outlet or the positions of a group of irrigation channel outlets.

8. The irrigation catheter device according to claim 6, wherein the closing element is made of high-grade, flexible material.

9. The irrigation catheter device according to claim 6, further comprising a force-transmission element, in the form of a wire or tube, attached to a proximal end of the closing element for control thereof.

10. The irrigation catheter device according to claim 1, further comprising:

a separate comparison measurement channel, which extends from the distal end region to the proximal end of the catheter body, and a comparison pressure sensor assigned to the separate comparison measurement channel for detection of an internal pressure value of a vessel and/or hollow organ.

11. The irrigation catheter device according to claim 1, wherein each irrigation catheter sensor is designed to register the dynamic pressure and/or the lumen sensor is designed to register the static pressure.

12. The irrigation catheter device according to claim 1, wherein a particular measuring transducer of the sensor, or at least a portion of the sensor, is disposed on a proximal end of the catheter body outside of the patient.

13. An ablation system comprising:

an irrigation catheter device in the form of an ablation catheter, according to claim 1; and a control device comprising a processing and display device, wherein the evaluation means of the irrigation catheter device are connected to the processing and display device of the control device, which is designed to process the evaluation results for determination of the quality of the tissue contact of an ablation element of the ablation catheter, and to provide a corresponding display.

14. The irrigation catheter device according to claim 1, wherein the plurality of irrigation channels each have a different diameter and/or length depending on the orientation of the distal end region.

15. The irrigation catheter device according to claim 3, wherein the plurality of irrigation channels each have a different diameter and/or length depending on the orientation of the distal end region.

16. The irrigation catheter device according to claim 5, wherein the plurality of irrigation channels each have a different diameter and/or length depending on the orientation of the distal end region.

* * * * *